United States Patent [19]
Schiessl et al.

[11] Patent Number: 5,869,678
[45] Date of Patent: Feb. 9, 1999

[54] OXIDATION OF PYRIDINE AND DERIVATIVES

[75] Inventors: Henry W. Schiessl, Northford; Steven A. Manke, Wallingford, both of Conn.

[73] Assignee: Olin Corporation, Cheshire, Conn.

[21] Appl. No.: 794,107

[22] Filed: Feb. 3, 1997

Related U.S. Application Data

[60] Provisional application No. 60/015,133 Mar. 29, 1996.
[51] Int. Cl.⁶ ...................... C07D 211/72; C07D 211/84; C07D 213/61; C07D 211/82
[52] U.S. Cl. ........................... 546/345; 546/348; 521/30; 521/33; 521/37
[58] Field of Search ..................................... 546/345, 348; 521/30, 33, 37

[56] References Cited

U.S. PATENT DOCUMENTS

| | | | |
|---|---|---|---|
| 3,047,579 | 7/1962 | Witman | 546/153 |
| 3,203,957 | 8/1965 | Kirchner | 546/345 |
| 4,504,666 | 3/1985 | Earl | 546/345 |
| 4,585,871 | 4/1986 | Boudakian | 546/345 |
| 5,082,940 | 1/1992 | Legrand | 544/353 |

*Primary Examiner*—D. Margaret M. Mach
*Attorney, Agent, or Firm*—Dale Lynn Carlson; Wiggin & Dana

[57] ABSTRACT

A process for preparing an N-oxide of pyridine or a halopyridine, said process comprising reacting a reaction mixture of said pyridine, or said halopyridine, and hydrogen peroxide in a reaction conducted at an elevated temperature in the presence of a catalytically effective amount of a heterogeneous catalyst, said heterogeneous catalyst being insoluble in said reactants, to form said 2-halopyridine-N-oxide or pyridine-N-oxide.

16 Claims, No Drawings

OXIDATION OF PYRIDINE AND DERIVATIVES

This application claims priority to Provisional application 60/015,133, filed 29 Mar. 1996.

FIELD OF THE INVENTION

This invention relates generally to the oxidation of pyridine and its derivatives and, more specifically, to the oxidation of pyridine and halopyridines to produce the corresponding N-oxide utilizing a supported or unsupported heterogeneous catalyst (i.e., one that is essentially insoluble in the reaction medium).

BACKGROUND OF THE INVENTION

Certain processes for producing 2-chloropyridine-N-oxide from 2-chloropyridine are well known. Illustrative prior art processes relate to the oxidation of 2-chloropyridine with hydrogen peroxide in the presence of homogeneous catalysts(s), such as tungstates, molybdates, and the like. As another illustration, U.S. Pat. No. 3,047,579 discloses soluble peroxy carboxylic acid catalysts for use in the preparation of N-oxides of tertiary organic bases, including halo-pyridine N-oxides.

The use of homogeneous catalysts for the oxidation of 2-chloropyridine, and other pyridine compounds, has the attendant disadvantage that the catalyst must be removed from the product stream and then recovered in reusable form. To achieve this recovery and reusability requires a number of steps, such as precipitation of the catalyst, filtration to separate the precipitated catalyst from the filtrate, and then reconversion of the precipitate back to its original catalytic form. These steps add considerably to the cost of producing the desired 2-chloropyridine-N-oxide product.

There are other costs and additional process complexities that make the use of soluble catalysts in homogeneous systems even more disadvantageous. For example, in such systems, the reaction is typically stopped using a quenching agent. The reaction between the soluble catalyst(s) and the quenching agent typically results in the formation of an insoluble product which is then typically removed by filtration using a filter aid.

Unfortunately, the use of the quenching agent and/or the filter aid increase the likelihood of introducing undesirable impurities into the desired 2-chloropyridine-N-oxide product. Accordingly, new processes for producing 2-chloropyridine-N-oxide that do not use a homogeneous catalyst system, do not employ a quenching agent, do not employ filter aid(s), and employ fewer process steps than prior art processes employing soluble catalysts, would be highly desired by, for example, the biocides intermediates manufacturing community. The present invention provides one such process.

SUMMARY OF THE INVENTION

In one aspect, the present invention relates to a process for preparing an N-oxide of pyridine or a halopyridine, said process comprising reacting a reaction mixture of said pyridine, or said halopyridine, and hydrogen peroxide in a reaction conducted at an elevated temperature in the presence of a catalytically effective amount of a heterogeneous catalyst, said heterogeneous catalyst being insoluble in said reactants, to form said 2-halopyridine-N-oxide or pyridine-N-oxide.

In another aspect, the present invention relates to a process for oxidizing pyridine or a substituted pyridine compound, to produce an N-oxide thereof, which comprises reacting said pyridine or substituted pyridine with hydrogen peroxide in a reaction conducted in the presence of a supported sulfonic acid or carboxylic acid catalyst, said supported catalyst comprising (and advantageously consisting essentially of) sulfonic acid or carboxylic acid moieties bound to an organic or inorganic substrate, said reaction being effected at a temperature of between about 50° C. and about 90° C. (preferably between 70° C. and 90° C.) using a molar ratio of said hydrogen peroxide to said pyridine or substituted pyridine of between 1:1 and 4:1, to produce said N-oxide.

In yet another aspect, the present invention relates to a process for producing 2-chloropyridine-N-oxide which comprises reacting 2-chloropyridine with hydrogen peroxide in a reaction conducted in the presence of a supported sulfonic acid or carboxylic acid catalyst, said supported catalyst comprising (and advantageously consisting essentially of) sulfonic acid or carboxylic acid moieties bound to an organic or inorganic substrate, said reaction being effected at a temperature of between about 50° C. and about 90° C. (preferably between 70 degrees Centigrade and 90° C.) using a molar ratio of said hydrogen peroxide to said pyridine or substituted pyridine of between 1:1 and 4:1, to produce said 2-chloropyridine-N-oxide.

In still another aspect, the present invention relates to a process for producing 2-chloropyridine-N-oxide which comprises the steps of:

(a) reacting 2-chloropyridine with hydrogen peroxide in a reaction conducted in the presence of a supported sulfonic acid or carboxylic acid catalyst, said supported catalyst comprising (and advantageously consisting essentially of) sulfonic acid or carboxylic acid moieties bound to an organic or inorganic substrate, said reaction being effected at a temperature of between about 50° C. and about 90° C. (preferably between 70° C. and 90° C.) using a molar ratio of said hydrogen peroxide to said 2-chloropyridine of between 1:1 and 4:1, to produce said 2-chloropyridine-N-oxide, and (b) separating said supported catalyst from said 2-chloropyridine-N-oxide in order to stop said reaction after a desired conversion to said 2-chloropyridine-N-oxide has been obtained.

These and other aspects will become apparent based upon reading the following detailed description of the invention.

DETAILED DESCRIPTION OF THE INVENTION

It has now been surprisingly found in accordance with the present invention that certain heterogeneous catalysts are useful for the oxidation of pyridines with hydrogen peroxide. Desirably, the heterogeneous catalysts are catalysts either bound to an organic or inorganic support, or are insoluble compositions that function as catalysts for the desired oxidation of pyridine or substituted pyridine. In this latter category, it has now been found, in accordance with one aspect of the present invention, that polymeric ion exchange resins can be used as heterogenous catalysts, or as supports for heterogeneous catalysts, in the desired oxidation reaction. Both anionic and cationic exchange resins are suitably employed in the processes of the present invention.

Particularly advantageous ion exchange resins are cation exchange resins containing repeating carboxylic acid and/or sulfonic acid groups which are effective in the reaction of pyridine or halopyridine with hydrogen peroxide to form the N-oxide derivative. The carboxylic acid or sulfonic acid groups are suitably bound (e.g., covalently attached) to the substrate or incorporated into the resin itself during preparation of the substrate. Most preferred are substrates containing the sulfonic acid group.

Alternatively, anionic exchange resins are suitably employed as substrates to bind homogeneous catalyst(s), such as tungstates, molybdates, and the like. Thus bound to a substrate, these otherwise-homogeneous catalysts become heterogeneous catalysts that are insoluble in the reaction medium in order to effect the oxidation of a pyridine compound in accordance with the present invention.

Examples of commercial resins that contain sulfonic acid groups as built-in moieties include those resins commercially available under the following trademarks: AMBERLYST XN-1010 and AMBERLYST 15, trademarks of Rohm and Haas; NAFION NR-50, a trademark of DuPont; IONAC CFP-110, a trademark of Sybron.

Useful resins suitably comprise an organic polymer, such as polystyrene, polyacrylate, divinyl benzene, fluorinated hydrocarbons, and combinations thereof.

In a broad aspect, the supported catalyst employed in the present invention comprises a catalyst on a support, or a support that provides built-in catalytic efficacy. The catalyst itself is employed in a "catalytically effective amount", i.e., an amount sufficient to catalyze the oxidation of the specific pyridine compound to the desired N-oxide. The support can be either an inorganic or organic substrate in any suitable configuration, such as beads, rods, macroreticulated sheets, and the like. An inorganic support is particularly advantageous since such a support is less likely to adversely affect the oxidation reaction being effected in accordance with the present invention.

Factors to be considered in selecting supports are: availability; cost; stability; ease of functionalization; particle size; surface area; pore diameter; and, pore volume. Suitable grades of aluminas, carbons, clays, glasses, silicas, and zeolites can be found which provide acceptable performance by many of these criteria. However, matrices composed of aluminum oxides (aluminas), silicon oxides (silicas) and chemical mixtures thereof, are most preferred because of their thermal and chemical stability, and the ease with which they can be functionalized. In addition, aluminas and, especially, silicas with desirable physical characteristics (particle size, surface area, pore diameter, and pore volume) are easily obtained.

The macroscopic form of the substrates that can be employed in the process of this invention can be varied significantly. The substrate can be utilized in the form of beads or powder or other relatively small particles. However, using the catalysts which are covalently bound to an insoluble inorganic matrix in the form of small beads is generally preferred since this simplifies removal of the bound catalyst through filtration and similar such techniques. Useful particle sizes are from 0.01 or smaller to 6 mm or larger.

The catalyst is employed in a catalytically effective amount, that is an amount sufficient to cause the desired N-oxide to form under the batch, continuous or semi-batch reactor conditions selected. For example, in a batch operation, an amount of catalyst of between about 10 and about 70 grams (on a dry resin basis) per mole of halopyridine or pyridine reactant is suitably employed. Useful halopyridines are chloro-, bromo-, iodo- and fluoropyridines, although chloropyridine is the preferred halopyridine. In a continuous or semi-continuous operation, the catalyst bed size and the flow rate of the reactants are suitably selected in light of the specific process economics and production requirements involved.

The reaction in accordance with the process of the present invention is suitably conducted at an elevated temperature. The temperature selected is suitably sufficiently high to facilitate the desired oxidation reaction, but the temperature must be below the decomposition temperature of the hydrogen peroxide reactant. Preferably the reaction temperature is between about 50° C. and about 90° C., more preferably between 70° C. and 90° C. Preferably, the reaction is conducted at an acid pH, suitably in the range of between 1 and 7, and advantageously a pH of between 1 and 4 If desired, the reaction can be conducted at a neutral or basic pH of 7 or greater, although this is not desired since the product yield tends to be lower than might otherwise be desired. At a basic pH, the sulfonic acid groups of the catalyst are converted to sulfonate moieties, and the carboxylic acid groups of the catalyst are converted to carboxylate moieties.

The molar ratio of hydrogen peroxide to pyridine reactant is preferably between 1:1 and 4:1, to produce the desired N-oxide.

The reaction in accordance with the process of the present invention provides an excellent selectivity to the desired N-oxide. For example, when 2-chloropyridine is reacted with aqueous hydrogen peroxide in the presence of the catalyst in accordance with the present invention, a substantial amount of the 2-chloropyridine is converted to 2-chloropyridine N-oxide with a selectivity approaching 100%. Thus, when a methanolic solution of 2-chloropyridine containing AMBERLYST 15 catalyst was reacted at 80° C. with aqueous hydrogen peroxide, 36.3% of the chloropyridine was converted to the N-oxide, with a selectivity of essentially 100%.

The process of the present invention is suitably effected in a batch, continuous, or semicontinuous fashion. Benefits afforded by virtue of the process of the present invention, as compared to prior homogeneous catalyst processes, include the following: (a) simplified separation of the catalyst from a reaction mixture, (b) facile ability to recover and reuse the catalyst, as well as (c) the ready adaptability of these heterogeneous catalysts for use in static and flow reaction systems.

It is generally desirable that the particles of the matrices suitably comprising the catalyst support have relatively large surface areas available for functionalization. In part, this area is dependant on the average specific pore volume of the substrate particles and therefore it, also, should be relatively large. Useful surface areas are from 5 $m^2$/gram or less to 600 $m^2$/gram or more, with pore volumes from 0.5 $cm^3$/gram or less to 1.2 $cm^3$/gram or more.

The average pore diameter of the support is desirably at least large enough to facilitate intimate contact between the reactants and the active catalyst sites on the substrate, thus allowing the resulting N-oxide to migrate away from the catalytic site, making the site available for further reaction. Therefore, generally, larger pore diameters are preferred. Although the pore diameter can vary over a wide range, particularly suitable pore diameters are from 6 to 500 nm (60 to 5000 Angstroms).

The following examples are intended to illustrate, but in no way limit the scope of, the present invention.

EXAMPLES

Example 1

12 grams of IONAC® CFP-110 catalyst (i.e., a polystyrene sulfonic acid catalyst crosslinked with divinyl benzene)

in its H-form were charged into a stirred flask with 10 grams methanol and 22.8 grams of 2-chloropyridine. A 6% excess of 50% aqueous hydrogen peroxide was added to the flask over a 2.6 hour period, while maintaining the flask at a temperature of 80° C. After completing the addition of hydrogen peroxide, heat was applied to the flask to maintain a reaction temperature of 80° C., and the mixture was stirred at the same temperature for an additional 22 hours. The conversion of 2-chloropyridine to 2-chloropyridine-N-oxide was 33.8%, with a selectivity to the desired product of essentially 100%. Unreacted 2-chloropyridine may be recovered by distillation and reused in the next batch.

Example 2

Example 1 was repeated using 9 grams of NAFION™ NR50 resin (i.e., a perfluorinated ion exchange resin containing sulfonic acid functional groups) as a catalyst. This resin is a perfluorinated sulfonic acid produced by DuPont. The conversion of chloropyridine to the N-oxide was 22.4% with nearly 100% selectivity.

Example 3

Example 1 was repeated using 12 grams of AMBER-SEP® 200H resin (i.e., a polystyrene sulfonic acid catalyst crosslinked with divinyl benzene) as a catalyst. This resin is a strong acid cation exchange resin produced by Rohm and Haas. The conversion of chloropyridine to the desired N-oxide was 34.3%, providing essentially 100% selectivity to the desired product.

Example 4

In this example, a quaternary anion exchange resin was used as a heterogeneous catalyst carrier for tungsten ion. AMBERLITE® IR-410, (i.e., an anion exchange resin containing quaternary ammonium functional groups) chloride form (produced by Rohm and Haas) was contacted with an aqueous solution of an equimolar mixture of sodium tungstate and tungstic acid in order to exchange the chloride ion on the resin with the hydrogen tungstate ion. The Amberlite resin so treated was filtered from the tungstate-containing solution and washed twice with water. The wet resin beads had a tungsten content of 17.8%. This resin was then contacted with a methanolic solution of 2-chloropyridine and finally with hydrogen peroxide, as in the previous examples. After filtering off the resin, the liquid phase contained 45 ppm of dissolved tungsten, indicating that the tungstate ion remained on the AMBERLITE catalyst support and that the catalyst was acting heterogeneously, as desired. This catalyst was then contacted with an aqueous solution of 0.402 moles 2-chloropyridine acidified with 0.03 moles phosphoric acid, followed by the addition 0.539 moles of 50% aq. hydrogen peroxide over a period of 2 hours, at a temperature of 80° C. The mixture was reacted for an additional 5 hours at the same temperature. Approximately 12% of the 2-chloropyridine was converted to the desired N-oxide in a selectivity to this product of essentially 100%.

Example 5

Oxidation at a Basic pH

The procedure of Example 1 above was repeated using the same reactants and reaction apparatus, except that all of the sulfonic acid moieties of the catalyst were neutralized with aqueous sodium hydroxide to sulfonate moieties before adding the hydrogen peroxide. After a reaction time of 22 hours, there was a two percent conversion of chloropyridine to the corresponding N-oxide, and the final pH was 4.0.

While the invention has been described above with references to specific embodiments thereof, it is apparent that many changes, modifications and variations in the materials, arrangements of parts and steps can be made without departing from the inventive concept disclosed herein. Accordingly, the spirit and broad scope of the appended claims is intended to embrace all such changes, modifications and variations that may occur to one of skill in the art upon a reading of the disclosure. All patent applications, patents and other publications cited herein are incorporated by reference in their entirety.

Having thus described the invention, what is claimed is:

What is claimed is:

1. A process for preparing an N-oxide of pyridine or a halopyridine, said process comprising reacting a reaction mixture of said pyridine, or said halopyridine, and hydrogen peroxide, said reaction mixture being free of peroxyacetic acid, in a reaction conducted at an elevated temperature in the presence of a catalytically effective amount of a heterogeneous catalyst, said heterogeneous catalyst being insoluble in said reactants, to form said 2-halopyridine-N-oxide or pyridine-N-oxide wherein said catalyst comprises a number of functional groups sufficient to provide an amount of between about 0.01 and about 10 milliequivalents of catalytic sites per gram of substrate.

2. The process of claim 1 wherein said catalyst is employed in said reaction mixture in an amount of between about 10 and about 70 grams on a dry weight basis, per mole of said halopyridine or said pyridine.

3. A process for preparing an N-oxide of pyridine or a halopyridine, said process comprising reacting a reaction mixture of said pyridine, or said halopyridine, and hydrogen peroxide, said reaction mixture being free of peroxyacetic acid, in a reaction conducted at an elevated temperature in the presence of a catalytically effective amount of a heterogeneous catalyst, said heterogeneous catalyst being insoluble in said reactants, to form said 2-halopyridine-N-oxide or pyridine-N-oxide wherein said catalyst comprises catalytically active moieties bound to an inorganic support selected from the group consisting of aluminas, carbons, clays, glasses, silicas, and zeolites and combinations thereof.

4. A process for preparing an N-oxide of pyridine or a halopyridine, said process comprising reacting a reaction mixture of said pyridine, or said halopyridine, and hydrogen peroxide, said reaction mixture being free of peroxyacetic acid, in a reaction conducted at an elevated temperature in the presence of a catalytically effective amount of a heterogeneous catalyst, said heterogeneous catalyst being insoluble in said reactants, to form said 2-halopyridine-N-oxide or pyridine-N-oxide wherein said catalyst comprises catalytically active moieties bound to an organic resin.

5. The process of claim 4 wherein said organic resin is selected from the group consisting of polystyrene, polyacrylate, divinylbenzene, fluorinated hydrocarbons, and combinations thereof.

6. A process for oxidizing pyridine or a substituted pyridine compound, to produce an N-oxide thereof, which comprises reacting said pyridine or substituted pyridine with hydrogen peroxide in a reaction conducted in the presence of a supported sulfonic acid or carboxylic acid catalyst, said supported catalyst comprising sulfonic acid or carboxylic acid moieties bound to an organic or inorganic substrate, said reaction being effected in the absence of peroxyacetic acid at a temperature of between about 50° C. and about 90° C. using a molar ratio of said hydrogen peroxide to said pyridine or substituted pyridine of between 1:1 and 4:1, to produce said N-oxide.

7. The process of claim 6 wherein said supported catalyst comprises a number of functional groups sufficient to provide an amount of between about 0.01 and about 10 milliequivalents of catalytic sites per gram of substrate.

8. The process of claim 6 wherein said supported catalyst is employed in said reaction mixture in an amount of between about 10 and about 70 grams on a dry weight basis, per mole of said halopyridine or said pyridine.

9. The process of claim 6 wherein said supported catalyst comprises catalytically active moieties bound to an inorganic support selected from the group consisting of aluminas, carbons, clays, glasses, silicas, and zeolites and combinations thereof.

10. The process of claim 6 wherein said supported catalyst comprises catalytically active moieties bound to an organic resin.

11. The process of claim 6 wherein said supported catalyst is bound to an organic substrate is selected from the group consisting of polystyrene, polyacrylate, divinylbenzene, fluorinated hydrocarbons, and combinations thereof.

12. The process of claim 6 wherein said catalyst consists essentially of sulfonic acid moieties, carboxylic acid moieties, and combinations thereof.

13. The process of claim 6 wherein said temperature for said reaction is between 70° C. and 90° C.

14. A process for producing 2-chloropyridine-N-oxide which comprises reacting 2-chloropyridine with hydrogen peroxide in a reaction conducted in the presence of a supported sulfonic acid or carboxylic acid catalyst and in the absence of peroxyacetic acid, said supported catalyst comprising sulfonic acid or carboxylic acid moieties bound to an organic or inorganic substrate, said reaction being effected at a temperature of between about 50° C. and about 90° C. using a molar ratio of said hydrogen peroxide to said pyridine or substituted pyridine of between 1:1 and 4:1, to produce said 2-chloropyridine-N-oxide.

15. A process for producing 2-chloropyridine-N-oxide which comprises the steps of:

(a) reacting 2-chloropyridine with hydrogen peroxide in a reaction conducted in the presence of a supported sulfonic acid or carboxylic acid catalyst and in the absence of peroxyacetic acid, said supported catalyst comprising sulfonic acid or carboxylic acid moieties bound to an organic or inorganic substrate, said reaction being effected at a temperature of between about 50° C. and about 90° C. using a molar ratio of said hydrogen peroxide to said 2-chloropyridine of between 1:1 and 4:1, to produce said 2-chloropyridine-N-oxide, and (b) separating said supported catalyst from said 2-chloropyridine-N-oxide in order to stop said reaction after a desired conversion to said 2-chloropyridine-N-oxide has been obtained.

16. The process of claim 15 wherein said catalyst has between 0.1 and 10 milliequivalents of said sulfonic acid or carboxylic acid moieties per gram of said substrate, said substrate being essentially insoluble in said reaction medium and having a pore diameter of between 6 and 500 nanometer, and a surface area of between 5 and 600 square meters per gram and a pore volume of between 0.5 and 1.2 cubic centimeters per gram of said support.

* * * * *